(12) United States Patent
Hsieh

(10) Patent No.: US 8,741,288 B2
(45) Date of Patent: Jun. 3, 2014

(54) PROTEIN MARKERS FOR DETECTING LIVER CANCER AND METHOD FOR IDENTIFYING THE MARKERS THEREOF

(75) Inventor: Sen-Yung Hsieh, Taipei (TW)

(73) Assignee: Chang Gung Medical Foundation, Linkou Branch, Guishan Township (TW)

( * ) Notice: Subject to any disclaimer, the term of this patent is extended or adjusted under 35 U.S.C. 154(b) by 131 days.

(21) Appl. No.: 12/831,447

(22) Filed: Jul. 7, 2010

(65) Prior Publication Data

US 2012/0009596 A1 Jan. 12, 2012

(51) Int. Cl.
*C07K 5/00* (2006.01)
*A61K 39/395* (2006.01)

(52) U.S. Cl.
USPC ........................................ 424/130.1; 530/350

(58) Field of Classification Search
None
See application file for complete search history.

(56) References Cited

U.S. PATENT DOCUMENTS

| | | | | |
|---|---|---|---|---|
| 5,480,968 A | * | 1/1996 | Kraus et al. | 530/326 |
| 7,449,559 B2 | * | 11/2008 | Ward et al. | 530/402 |
| 2009/0304693 A1 | * | 12/2009 | Ghayur et al. | 424/133.1 |
| 2011/0110852 A1 | * | 5/2011 | Miller et al. | 424/1.49 |

FOREIGN PATENT DOCUMENTS

| | | | |
|---|---|---|---|
| JP | 2009155329 | * | 7/2009 |
| WO | WO02/090580 A1 | | 11/2002 |

OTHER PUBLICATIONS

Chaib et al (Neoplasia 3:43-53, 2001).*
Fottner et al (European J Endocrinology 159:317-327, 2008).*
Chia Hua Chen, "An Interstitial fluid approach to discover biomarker candidates for human hepatocellular carcinoma," Jul. 2007 Taiwan. (Full Foreign Document + English Translation of Abstract Provided).
Wan Ru Chen, "Aberrant activation of ErbB3 via a novel autocrine mechanism in human hepatocellular carcinoma," Jul. 2008 Taiwan. (Full Foreign Document + English Translation of Abstract Provided).

* cited by examiner

*Primary Examiner* — Lei Yao
(74) *Attorney, Agent, or Firm* — Ascenda Law Group PC

(57) ABSTRACT

The present invention relates to the diagnosis of liver cancer. It discloses the use of protein ERBB3 and protein IGFBP2 in the diagnosis of liver cancer. It relates to a method for diagnosis of liver cancer from a liquid sample, derived from an individual by measuring ERBB3 protein and IGFBP2 protein in the sample. Measurement of ERBB3 protein and IGFBP2 protein can, e.g., be used in the early detection or diagnosis of liver cancer.

8 Claims, 15 Drawing Sheets

SEQUENCE LISTING

```
<160> NUMBER OF SEQ ID NOS: 4

<210> SEQ ID NO 1
<211> LENGTH: 1342
<212> TYPE: PRT
<213> ORGANISM: Homo sapiens

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140
```

-continued

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
                260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
                340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
                500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys

```
                565                 570                 575
Ala His Phe Arg Asp Gly Pro His Cys Val Ser Cys Pro His Gly
            580                 585                 590

Val Leu Gly Ala Lys Gly Pro Ile Tyr Lys Tyr Pro Asp Val Gln Asn
                595                 600                 605

Glu Cys Arg Pro Cys His Glu Asn Cys Thr Gln Gly Cys Lys Gly Pro
            610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
                660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
            690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
            770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
            965                 970                 975

Val Ile Lys Arg Glu Ser Gly Pro Gly Ile Ala Pro Gly Pro Glu Pro
            980                 985                 990
```

His Gly Leu Thr Asn Lys Lys Leu Glu Glu Val Glu Leu Glu Pro Glu
            995                1000                1005

Leu Asp Leu Asp Leu Asp Leu Glu Ala Glu Glu Asp Asn Leu Ala Thr
    1010                1015                1020

Thr Thr Leu Gly Ser Ala Leu Ser Leu Pro Val Gly Thr Leu Asn Arg
1025                1030                1035                1040

Pro Arg Gly Ser Gln Ser Leu Leu Ser Pro Ser Ser Gly Tyr Met Pro
                1045                1050                1055

Met Asn Gln Gly Asn Leu Gly Glu Ser Cys Gln Ser Ala Val Ser
                1060                1065                1070

Gly Ser Ser Glu Arg Cys Pro Arg Pro Val Ser Leu His Pro Met Pro
            1075                1080                1085

Arg Gly Cys Leu Ala Ser Glu Ser Ser Glu Gly His Val Thr Gly Ser
        1090                1095                1100

Glu Ala Glu Leu Gln Glu Lys Val Ser Met Cys Arg Ser Arg Ser Arg
1105                1110                1115                1120

Ser Arg Ser Pro Arg Pro Arg Gly Asp Ser Ala Tyr His Ser Gln Arg
                1125                1130                1135

His Ser Leu Leu Thr Pro Val Thr Pro Leu Ser Pro Pro Gly Leu Glu
            1140                1145                1150

Glu Glu Asp Val Asn Gly Tyr Val Met Pro Asp Thr His Leu Lys Gly
            1155                1160                1165

Thr Pro Ser Ser Arg Glu Gly Thr Leu Ser Ser Val Gly Leu Ser Ser
    1170                1175                1180

Val Leu Gly Thr Glu Glu Glu Asp Glu Asp Glu Glu Tyr Glu Tyr Met
1185                1190                1195                1200

Asn Arg Arg Arg Arg His Ser Pro Pro His Pro Pro Arg Pro Ser Ser
                1205                1210                1215

Leu Glu Glu Leu Gly Tyr Glu Tyr Met Asp Val Gly Ser Asp Leu Ser
                1220                1225                1230

Ala Ser Leu Gly Ser Thr Gln Ser Cys Pro Leu His Pro Val Pro Ile
        1235                1240                1245

Met Pro Thr Ala Gly Thr Thr Pro Asp Glu Asp Tyr Glu Tyr Met Asn
    1250                1255                1260

Arg Gln Arg Asp Gly Gly Gly Pro Gly Gly Asp Tyr Ala Ala Met Gly
1265                1270                1275                1280

Ala Cys Pro Ala Ser Glu Gln Gly Tyr Glu Glu Met Arg Ala Phe Gln
                1285                1290                1295

Gly Pro Gly His Gln Ala Pro His Val His Tyr Ala Arg Leu Lys Thr
                1300                1305                1310

Leu Arg Ser Leu Glu Ala Thr Asp Ser Ala Phe Asp Asn Pro Asp Tyr
        1315                1320                1325

Trp His Ser Arg Leu Phe Pro Lys Ala Asn Ala Gln Arg Thr
    1330                1335                1340

<210> SEQ ID NO 2
<211> LENGTH: 624
<212> TYPE: PRT
<213> ORGANISM: Homo sapiens

<400> SEQUENCE: 2

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

-continued

```
Leu Tyr Glu Arg Cys Glu Val Met Gly Asn Leu Glu Ile Val Leu
         35                  40                  45
Thr Gly His Asn Ala Asp Leu Ser Phe Leu Gln Trp Ile Arg Glu Val
 50                  55                  60
Thr Gly Tyr Val Leu Val Ala Met Asn Glu Phe Ser Thr Leu Pro Leu
 65                  70                  75                  80
Pro Asn Leu Arg Val Val Arg Gly Thr Gln Val Tyr Asp Gly Lys Phe
                 85                  90                  95
Ala Ile Phe Val Met Leu Asn Tyr Asn Thr Asn Ser Ser His Ala Leu
                100                 105                 110
Arg Gln Leu Arg Leu Thr Gln Leu Thr Glu Ile Leu Ser Gly Gly Val
            115                 120                 125
Tyr Ile Glu Lys Asn Asp Lys Leu Cys His Met Asp Thr Ile Asp Trp
130                 135                 140
Arg Asp Ile Val Arg Asp Arg Asp Ala Glu Ile Val Val Lys Asp Asn
145                 150                 155                 160
Gly Arg Ser Cys Pro Pro Cys His Glu Val Cys Lys Gly Arg Cys Trp
                165                 170                 175
Gly Pro Gly Ser Glu Asp Cys Gln Thr Leu Thr Lys Thr Ile Cys Ala
            180                 185                 190
Pro Gln Cys Asn Gly His Cys Phe Gly Pro Asn Pro Asn Gln Cys Cys
        195                 200                 205
His Asp Glu Cys Ala Gly Gly Cys Ser Gly Pro Gln Asp Thr Asp Cys
210                 215                 220
Phe Ala Cys Arg His Phe Asn Asp Ser Gly Ala Cys Val Pro Arg Cys
225                 230                 235                 240
Pro Gln Pro Leu Val Tyr Asn Lys Leu Thr Phe Gln Leu Glu Pro Asn
                245                 250                 255
Pro His Thr Lys Tyr Gln Tyr Gly Gly Val Cys Val Ala Ser Cys Pro
            260                 265                 270
His Asn Phe Val Val Asp Gln Thr Ser Cys Val Arg Ala Cys Pro Pro
        275                 280                 285
Asp Lys Met Glu Val Asp Lys Asn Gly Leu Lys Met Cys Glu Pro Cys
290                 295                 300
Gly Gly Leu Cys Pro Lys Ala Cys Glu Gly Thr Gly Ser Gly Ser Arg
305                 310                 315                 320
Phe Gln Thr Val Asp Ser Ser Asn Ile Asp Gly Phe Val Asn Cys Thr
                325                 330                 335
Lys Ile Leu Gly Asn Leu Asp Phe Leu Ile Thr Gly Leu Asn Gly Asp
            340                 345                 350
Pro Trp His Lys Ile Pro Ala Leu Asp Pro Glu Lys Leu Asn Val Phe
        355                 360                 365
Arg Thr Val Arg Glu Ile Thr Gly Tyr Leu Asn Ile Gln Ser Trp Pro
370                 375                 380
Pro His Met His Asn Phe Ser Val Phe Ser Asn Leu Thr Thr Ile Gly
385                 390                 395                 400
Gly Arg Ser Leu Tyr Asn Arg Gly Phe Ser Leu Leu Ile Met Lys Asn
                405                 410                 415
Leu Asn Val Thr Ser Leu Gly Phe Arg Ser Leu Lys Glu Ile Ser Ala
            420                 425                 430
Gly Arg Ile Tyr Ile Ser Ala Asn Arg Gln Leu Cys Tyr His His Ser
        435                 440                 445
Leu Asn Trp Thr Lys Val Leu Arg Gly Pro Thr Glu Glu Arg Leu Asp
450                 455                 460
```

```
Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510

His Cys Asn Phe Leu Asn Gly Glu Pro Arg Glu Phe Ala His Glu Ala
        515                 520                 525

Glu Cys Phe Ser Cys His Pro Glu Cys Gln Pro Met Glu Gly Thr Ala
    530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
                580                 585                 590

Pro Cys His Glu Asn Cys Thr Gln Gly Cys Lys Gly Pro Glu Leu Gln
            595                 600                 605

Asp Cys Leu Gly Gln Thr Leu Val Leu Ile Gly Lys Thr His Leu Thr
610                 615                 620
```

<210> SEQ ID NO 3
<211> LENGTH: 328
<212> TYPE: PRT
<213> ORGANISM: Homo sapiens

<400> SEQUENCE: 3

```
Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Arg Val Ala Pro Pro
    50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
    130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220
```

-continued

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Glu Ala Arg
305                 310                 315                 320

Gly Val Asp Thr Gln Arg Met Gln
                325

<210> SEQ ID NO 4
<211> LENGTH: 289
<212> TYPE: PRT
<213> ORGANISM: Homo sapiens

<400> SEQUENCE: 4

Glu Val Leu Phe Arg Cys Pro Pro Cys Thr Pro Glu Arg Leu Ala Ala
1               5                   10                  15

Cys Gly Pro Pro Arg Val Ala Pro Pro Ala Ala Val Ala Ala Val Ala
                20                  25                  30

Gly Gly Ala Arg Met Pro Cys Ala Glu Leu Val Arg Glu Pro Gly Cys
            35                  40                  45

Gly Cys Cys Ser Val Cys Ala Arg Leu Glu Gly Glu Ala Cys Gly Val
        50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
                100                 105                 110

Asn Gly Asp Asp His Ser Glu Gly Gly Leu Val Glu Asn His Val Asp
            115                 120                 125

Ser Thr Met Asn Met Leu Gly Gly Gly Ser Ala Gly Arg Lys Pro
130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                165                 170                 175

Glu Glu Pro Lys Lys Leu Arg Pro Pro Pro Ala Arg Thr Pro Cys Gln
            180                 185                 190

Gln Glu Leu Asp Gln Val Leu Glu Arg Ile Ser Thr Met Arg Leu Pro
        195                 200                 205

Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

```
                            -continued
Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Glu Ala Arg Gly Val Asp Thr Gln Arg Met
        275                 280                 285

Gln
```

PROTEIN MARKERS FOR DETECTING LIVER CANCER AND METHOD FOR IDENTIFYING THE MARKERS THEREOF

FIELD OF THE INVENTION

The present invention, relates to, protein markers for detecting liver cancer, also called hepatoma, in plasma or serum and a method for detecting liver cancer thereof. The present invention also relates to a method for identifying a novel marker in plasma/serum for detecting liver cancer. In particular, the present invention relates to protein markers expressed in tissue interstitial fluid and a method for identifying novel marker in a tissue interstitial fluid for detecting liver cancer. Especially, the present invention relates to plasma/serums ERBB3 and IGFBP2 protein markers used for detecting liver cancer precisely.

BACKGROUND OF THE INVENTION

Cancer remains a major public health challenge despite progress in detection and therapy. Whole blood, serum, plasma, or nipple aspirate fluid are the most widely used sources of sample in clinical routine. Conventionally, researchers try to find valuable markers from plasma/serum to detect liver cancer. However, up to 90 percentage of the plasma/serum are composed by 6 constant serum proteins, and 99 percentage are composed by about 20 constant proteins. The metabolic and the physiological conditions could be represented in whole blood, serum or plasma. Some specific proteins with diagnosis values are secreted into whole blood, serum or plasma, but they always present in a trace amount and are hard to be found. Therefore, an urgent clinical need exists to improve the method to identify biomarkers for the diagnosis of liver cancer from plasma/serum.

Some researchers tried to find tumor markers from hepatocellular carcinoma (hereinafter may be referred to as "liver cancer", "hepatoma" or "HCC") tissue or cell culture media. However, neither tumor tissues nor cell culture media of hepatocellular carcinoma has been proved to be an adequate source for identifying new serum markers for hepatoma. In contrast, the tissue interstitial fluid is the media between tumor cells and the circulation, and tumor interstitial fluid represents the microenvironment that tumor cells inhabit. Tumor markers shed into circulation may also be generated by interaction of tumor cells with its microenvironment. It is, therefore, tempting to examine whether tumor interstitial fluid is the source for discovery of serum biomarkers.

So far, some markers, including alpha-fetoprotein (AFP), alpha-fetoprotein lectin fraction-L3 fraction, PIVKA-II, AFU and GPC3, have conventionally been employed for liver cancer diagnosis. However, results obtained from detecting by the foregoing tumor markers often show false-positive or false-negative, so that their functions of detection are limited clinically. Despite the large and ever growing list of candidate protein markers in the field of liver cancer, to date clinical/diagnostic utility of these molecules is not known. In order to be of clinical utility, a new diagnostic marker as a single marker should be at least as good at the best single marker known in the art. Or, a new marker should lead to a progress in diagnostic sensitivity and/or specificity either if used alone or in combination with one or more other markers, respectively.

Therefore, there is a keen need in the art to develop a new tumor marker for clinical diagnosis and increase the precision of diagnosis. It was the task of the present invention to investigate whether a new marker can be identified which may aid in liver cancer diagnosis. Surprisingly, it has been found that use of the marker ERBB3 or IGFBP2 can at least partially overcome the problems known from the state of the art.

SUMMARY OF THE INVENTION

The present invention therefore relates to a novel protein marker ERBB3 for detecting liver cancer.

The present invention therefore relates to a novel protein marker IGFBP2 for detecting liver cancer.

The present invention therefore relates to a method for the detection of liver cancer comprising the steps of a) providing a liquid sample obtained from an individual, b) contacting said sample with a specific binding agent for ERBB3 or IGFBP2 under conditions appropriate for formation of a complex between said binding agent and ERBB3 or IGFBP2, and c) correlating the amount of complex formed in (b) to the detection of liver cancer.

The present invention also relates to a method for identifying a marker for detecting liver tumor in plasma/serum, comprising:

obtaining fresh tissues of liver cancer and non-cancer liver tissues from patients with liver cancer, cutting the tissues and washing by PBS solution twice, culturing the cut tissues in an incubator for 10 minutes, and then precipitating by centrifugation at 1000-2000 rpm/min for 2-5 minutes to obtain cell pellets and removing the contaminations;

re-suspending the cell pellets in PBS solution, culturing the suspended cells in PBS solution in the incubator for 60 minutes, precipitating by centrifugation at 1000-2000 rpm/min for 2-5 minutes to remove cell pellets and obtain a crude tissue interstitial fluid;

centrifugating the crude tissue interstitial fluids by centrifugation at 5000-15000 rpm/min for 15-30 minutes to remove undissolved cell matrix and obtain a pure tissue interstitial fluid;

comparing the difference of the protein components between the tissue interstitial fluids obtained from the liver cancer tissues and non-cancer liver tissues by proteomic methods, then identifying the relatively high-content proteins in tissue fluids of the liver cancer cells, and listing those relatively high-content proteins as candidate biomarkers for hepatoma detection;

detecting the candidate biomarkers in serum by ELISA and measuring the concentrations of the candidate markers, and analyzing the concentrations difference by student t-test analysis and Receiver Operating Characteristic curve (ROC curve) to check the function of the candidate biomarkers.

The candidate biomarkers were further used to detect serum samples obtained from liver cancer patients and, non-liver cancer patients by ELISA and ROC curve. When area under curve values (AUC values) of the candidate markers in serums are greater than 90%, the protein is classified as suitable markers for hepatoma detection.

Comparing with the conventional method of detecting liver cancer, it is hard to find a suitable marker from serum for detecting liver cancer by the conventional methods. The present invention provides a novel ERBB3 protein and a novel IGFBP2 protein as markers for liver cancer detection. ERBB3 protein and IGFBP2 protein are found from tissue interstitial fluids and have been proven their powerful functions in identifying liver cancers. Detection by the concentrations of ERBB3 protein and IGFBP2 protein in patients' serum/plasma or whole blood could increase the sensitivity of liver cancer diagnosis.

As a skilled artisan will appreciate, any such diagnosis is made in vitro. The patient sample is discarded afterwards. The patient sample is merely used for the in vitro diagnostic method of the invention and the material of the patient sample is not transferred back into the patient's body. Typically, the sample is a liquid sample.

A specific binding agent preferably is an antibody reactive with ERBB3 or IGFBP2. The term antibody refers to a polyclonal antibody, a monoclonal antibody, fragments of such antibodies, as well as to genetic constructs comprising the binding domain of an antibody. Any antibody fragment retaining the above criteria of a specific binding agent can also be used.

In a preferred embodiment the method according to the present invention is practiced with serum as liquid sample material.

In a further preferred embodiment the method according to the present invention is practiced with plasma as liquid sample material.

In a further preferred embodiment the method according to the present invention is practiced with whole blood as liquid sample material.

In a further preferred embodiment the method according to the present invention is practiced with tissue interstitial fluid of liver as liquid sample material.

Whereas application of routine proteomics methods to tissue interstitial fluid obtained from tissue samples, leads to the identification of many potential marker candidates for the tissue selected, the inventors of the present invention have been able to surprisingly detect both or one of ERBB3 and IGFBP2 in a bodily fluid sample. Even more surprising they have been able to demonstrate that the presence of ERBB3 and IGFBP2 in such liquid sample obtained from an individual can be correlated to the diagnosis of liver cancer.

Antibodies to ERBB3 and IGFBP2 with great advantages can be used in established procedures, e.g., to detect liver cancer cells in situ, in biopsies, or in immunohistological procedures.

Preferably, an antibody to ERBB3 is used in a qualitative (ERBB3 present or absent) or quantitative (ERBB3 amount is determined) immunoassay.

Preferably, an antibody to IGFBP2 is used in a qualitative (IGFBP2 present or absent) or quantitative (IGFBP2 amount is determined) immunoassay.

Measuring the level of protein ERBB3 or IGFBP2 has proven very advantageous in the field of liver cancer. Therefore, in a further preferred embodiment, the present invention relates to use of protein ERBB3 or/and IGFBP2 as a marker molecule in the diagnosis of liver cancer from a liquid sample obtained from an individual.

The details of one or more embodiments of the technology are set forth in the accompanying drawings and the description below. Other features, objects, and advantages of the technology will be apparent from the description and drawings, and from the claims. All cited patents, and patent applications and references (including references to public sequence database entries) are incorporated by reference in their entireties for all purposes.

DETAILED DESCRIPTION OF THE INVENTION

The following examples illustrate the invention without limiting its scope.

The present invention relates to a method for the detection of liver cancer, comprising the steps of:

a) providing a liquid sample obtained from an individual, b) contacting said sample with an antibody specific for at least one of ERBB3 protein(SEQ ID NO:2) and IGFBP2 protein(SEQ ID NO: 4) under conditions appropriate for formation of a complex between said antibody and at least one of said proteins, and c) correlating an amount of the complex formed in (b) to the detection of liver cancer.

Figure 1:
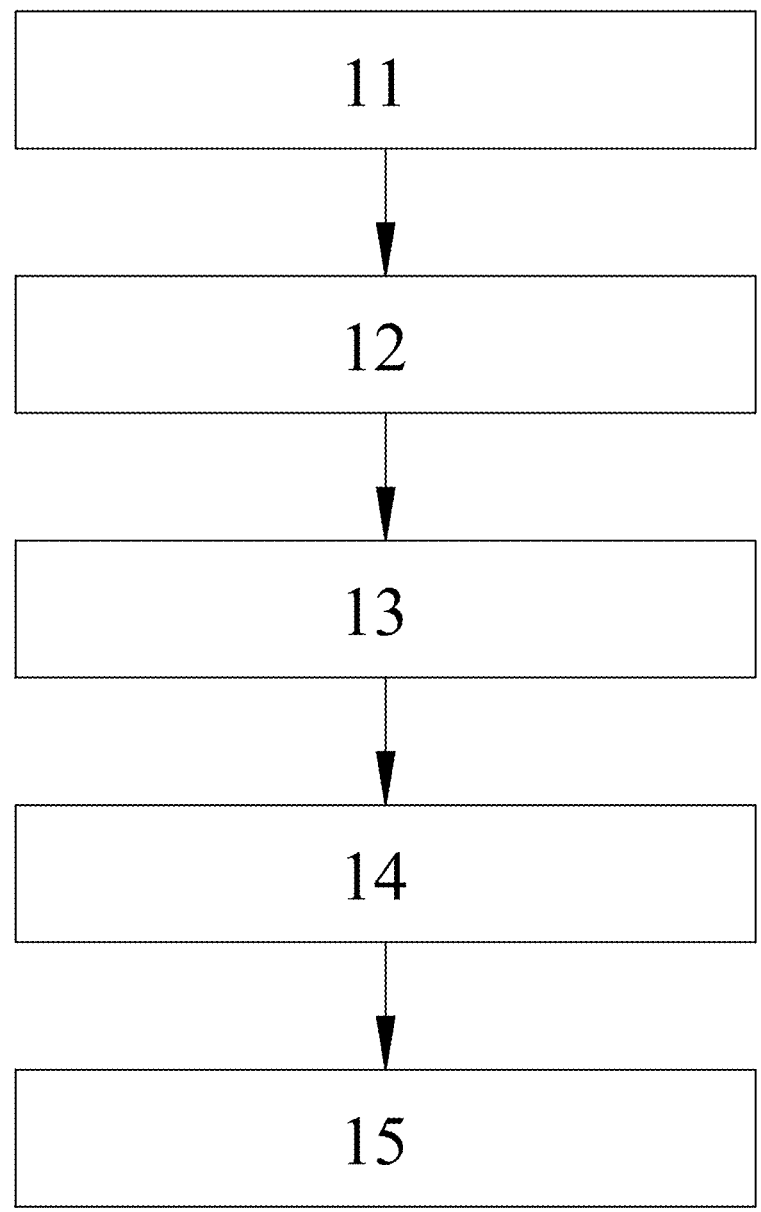
FIG. 1 is a scheme showing steps performing in accordance with the present invention.

With reference to FIG. 1, the method for obtaining the novel ERBB3 and IGFBP2 protein markers for hepatoma detection comprises the steps of:

Step 1 (11) Obtaining liver cancer tissues and non-cancer liver tissues from individuals respectively:
  cutting the obtained liver cancer tissues and the non-cancer liver tissues into 1×1×3 mm$^3$ pellets,
  washing the above pellets by PBS solution twice,
  incubating the cell pellets by PBS solution at 37° C., 10% $CO_2$ incubator for 10 minutes,
  centrifuging the cultured cell pellets at 1000 to 2000 rpm/min for 2 to 5 minutes to remove the contaminations on liver cancer tissues and non-cancer liver tissues, Step 2 (12) Separating tissues and tissue interstitial fluid by low speed centrifugation:
  culturing the cell pellets by PBS at 37° C., 10% $CO_2$ incubator for 60 minutes,
  centrifuging the cultured broth at 1000-2000 rpm/min for 2-5 minutes to separate tissues and tissue interstitial fluid, and avoiding cell crack, Step 3 (13) Removing the dissolved matrix by high speed centrifugation,
  centrifuging the cultured broth by 5000-15000 rpm/min for 15-30 minutes to increase the purification and the sensitivity of the tissue interstitial fluid, Step 4 (14) Finding candidate biomarkers for hepatoma detection:
  comparing protein pattern obtained from liver cancer tissues and non-cancer liver tissues to select possible protein markers, said protein patterns may be performed such as 2-DE or antibody arrays,
  identifying and listing the candidate biomarkers which are present in relatively high concentration and are highly different in the protein pattern of the liver cancer and non-cancer liver tissues.

Step 5 (15) Selecting candidate biomarkers for hepatoma detection proteins:
  analyzing the candidate biomarkers by ELISA method and checking the concentrations of each candidate biomarker in cancer tissues and non-cancer tissues,
  analyzing the concentrations obtained from the above sub-step by student t-test to identify the concentration of the biomarker with significant difference, and selecting the concentration of the biomarker with p value<0.01,
  further analyzing the concentration with significant difference by ROC curve method and selecting the candidate biomarker with AUC value>90% as the biomarker for hepatoma detection.

In a preferred embodiment, the above selected markers were further analyzed by applying in the serum samples obtained from another liver cancer group and non-liver cancer group. The method may be performed by ELISA method and ROC curve method for getting their AUC values. When the AUC values>90%, the selected marker was confirmed to be a suitable marker for liver cancer detection.

As used herein, the term "non-liver cancer" refers to a patient that may have cirrhosis without liver cancer, chronic hepatitis or healthy individuals without liver cancer.

As used herein, "antibody" or "specific binding agent" includes immunoglobulin molecules and immunologically active determinants of immunoglobulin molecules, i.e., molecules that contain an antigen binding site which specifically binds (immunoreacts with) an antigen. Structurally, the simplest naturally occurring antibody (e.g., IgG) comprises four polypeptide chains, two copies of a heavy (H) chain and two of a light (L) chain, all covalently linked by disulfide bonds. Specificity of binding in the large and diverse set of antibodies is found in the variable (V) determinant of the H and L chains; regions of the molecules that are primarily structural are constant (C) in this set. Antibody includes polyclonal antibodies, monoclonal antibodies, whole immunoglobulins, and antigen binding fragments of the immunoglobulins.

In the diagnostic and prognostic assays of the invention, the antibody can be a polyclonal antibody or a monoclonal antibody and in a preferred embodiment is a labeled antibody.

In this exemplary method a Receiver Operating Characteristic curve (ROC curve) is generated. An ROC curve is a plot of test sensitivity (plotted on the y axis) versus its False Positive Rate (or 1—specificity) (plotted on the x axis). Each point on the graph is generated by using a different cut point. The set of data points generated from the different cut points is the empirical ROC curve. Lines are used to connect the points from all the possible cut points. The resulting curve illustrates how sensitivity and the FPR vary together. ROC is a standard statistical method used in the evaluation of a biomarker in disease diagnosis. This analysis determines the ability of a test to discriminate diseased cases from normal cases. The value of the area under the ROC curve is a measure of test accuracy.

EXAMPLE 1

Markers Selection 1-1 Sample Collection and Preparation

Step 1: Liver cancer tissues and non-cancer liver tissues were respectively collected from 10 patients with hepatoma received surgical resection of liver tumors. The contaminations on the liver cancer tissues and non-cancer liver tissues were removed by low speed centrifugation.

In a preferred embodiment of the present invention, liver cancer tissues and non-cancer liver tissues were obtained by surgical operation. The sizes of the tissues were cut as 1×1×3 mm, and then the cut tissues were cultured by PBS solution in an incubator at 37° C. and 10% $CO_2$ condition for 10 minutes. Then the culture broth was centrifuged at 1000-2000 rpm/min for 2-5 minutes for removing the contaminations on the tissues.

Step 2: Tissues and tissue interstitial fluid were separated by low speed centrifugation to obtain tissue interstitial fluid.

The cutting tissues were collected and further cultured by PBS solutions in an incubator at 37° C., 10% $CO_2$ condition for 60 minutes. Then the culture broths were centrifuged at 1000-2000 rpm/min for 2-5 minutes for removing cells to obtain a crude tissue interstitial fluid.

Step 3: The crude tissue interstitial fluid were centrifuged again to remove undissolved matrix by high speed centrifugation to obtain a pure tissue interstitial fluid.

To obtain pure tissue interstitial fluids respectively, from liver cancer tissues and non-cancer liver tissues, the crude tissue interstitial fluids were centrifuged at 5000-15000 rpm/min for 15-30 minutes to remove the undissolved matrix and obtain a pure tissue interstitial fluid.

Step 4: Candidate biomarkers for hepatoma detection were selected.

Figure 2A:
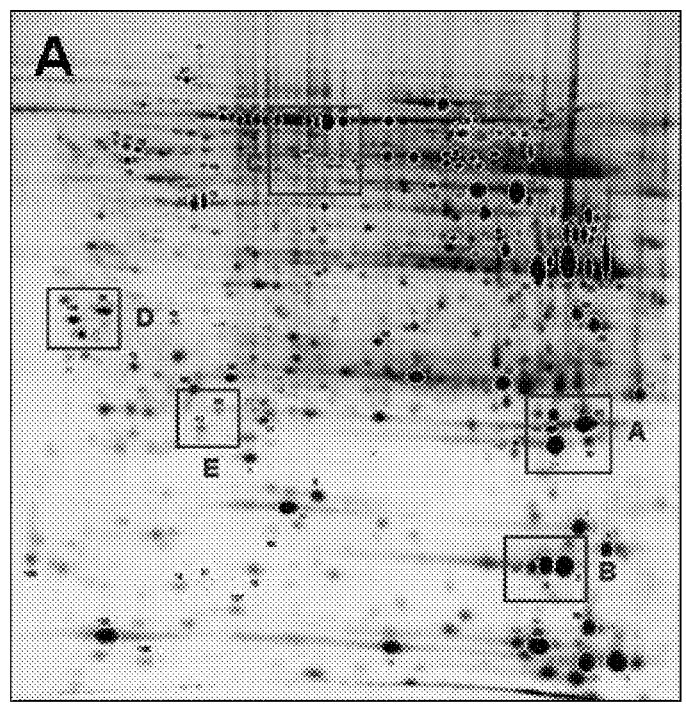
FIG. 2A is a picture showing a two-dimensional gel electrophoresis (2-DE) of Example 1 in accordance with the present invention.
Figure 2B:
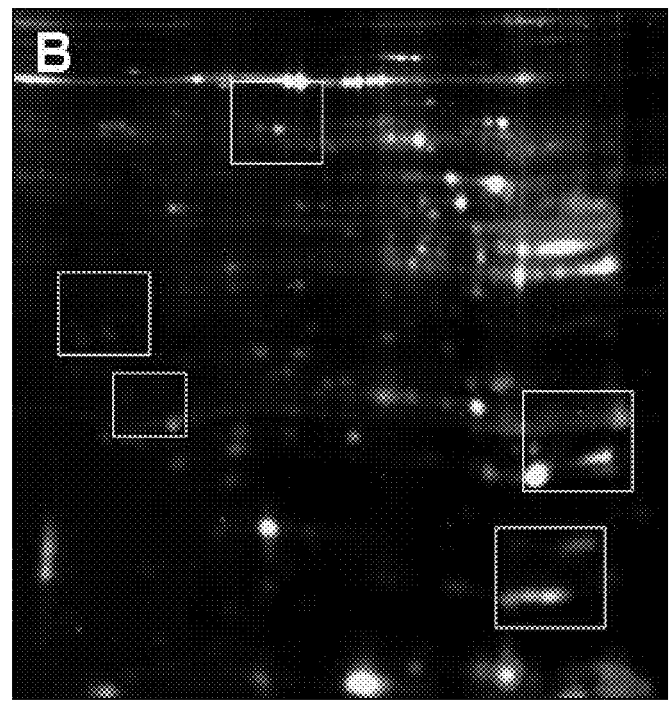
FIG. 2B is a picture showing a two-dimensional differential fluorescence gel electrophoresis (2-D DIGE) condition of Example 1 in accordance with the present invention.

The electropherograms of FIGS. 2A and 2B illustrate the unique 2-DE and 2-D DIGE patterns of the diseased (liver cancer) and normal (non-cancer liver) tissues. The representative images of two-dimensional gel electrophoresis (2-DE) (FIG. 2A) and two-dimensional differential fluorescence gel electrophoresis (2-D DIGE) (FIG. 2B). 2-DE was performed on immobilized pH 4-7 gradient strips, followed by the second-dimensional separation on 10-16% gradient polyacrylamide gels. For 2-DE, the separated proteins were stained with SYPRO Ruby. Images were captured, and relative volumes for each protein were normalized, matched across gels and determined with the aide of software analysis. For 2-D DIGS, equal amount of protein lysate from TIF (hepatoma interstitial fluid) and NIF (non-hepatoma interstitial fluid) were labeled with Cy3 and Cy5 dyes respectively, and vice versa, using the minimal labeling procedures. TIF and NIF were mixed together and then separated by 2-dimensional gel electrophoresis. Proteins with significant differentiation between TIF and NIF were selected for protein identification using mass spectrometry (matrix-assisted laser desorption/ionization time-of-flight/time-of-flight mass spectrometry, MALDI-TOF/TOF MS). Results showed that the concentrations of ERBB3 (v-erb-b2 erythroblastic leukemia viral oncogene homolog 3) protein and IGFBP2 (Insulin-like growth factor binding protein 2) protein in the tissue interstitial fluid of the liver cancer tissues were higher than them appeared in the tissue interstitial fluid of non-cancer liver tissues.

Furthermore, the tissue interstitial fluids obtained from liver cancer tissues and non-cancer liver tissues were also analyzed by Antibody Array (Human Cytokine Antibody Array G Series 2000, RayBiotech Inc.) method, comprising:

A. 100 mg tissue interstitial fluids were dropped on each reaction well of the array chip for reaction at room temperature for 2 hours.

B. The reaction wells were washed by washing solution for 5 times, and the blocking buffer was mixed well with antibodies which had linked with biotin.

C. The blocking buffer containing antibodies linked with biotin were added into each reaction wells at room temperature for 2 hours.

D. The blocking buffer containing antibodies linked with biotin were removed. Then the reaction wells were washed by washing solution for 5 times, and a diluted Cy3-conjugated streptavidin which was included in the kit were added for reacting in dark at room temperature for 2 hours.

E. The Cy3-conjugated streptavidin were removed and the reaction wells were washed again by washing solution for 5 times and dried in dark at room temperature.

Figure 3:
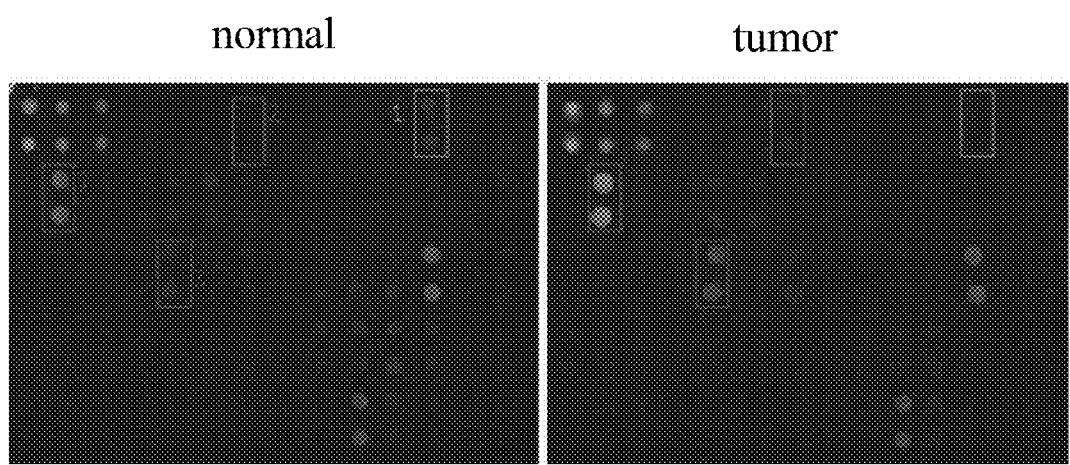
FIG. 3 is a picture showing results of normal tissue interstitial fluid and tumor tissue interstitial fluid on a biochip.

F. With reference to FIG. 3, the results showed on the protein array were read by Confocal Scanner Chip Reader. The strength of fluorescence showed on the protein array was further analyzed by Gene Pix Pro 4.1 software. Results showed that both concentrations of ERBB3 protein and IGFBP2 protein in the tissue interstitial fluids of the cancer tissues were higher than the non-cancer tissues. ERBB3 protein and IGFBP2 protein were selected as candidate biomarkers for hepatoma detection.

Complete amino acid sequence of ERBB3 protein was shown as SEQ ID NO: 1, and nature amino acid sequence in human serum was shown as SEQ ID NO: 2. Sequence of SEQ ID NO: 2 is same as the sequence from the 20 to 643 amino acid sequence of SEQ ID NO: 1. Complete amino acid sequence of IGFBP2 was shown as SEQ ID NO: 3, and nature amino acid sequence in human serum was shown as SEQ ID NO: 4. Sequence of SEQ ID NO: 4 is same as the sequence from the 40 to 328 amino acid sequence of SEQ ID NO: 3.

Step 5: The candidate biomarkers were used for hepatoma detection

A. Detect the concentrations of ERBB3 protein and IGFBP2 protein in serum:

To measure the concentration of ERBB3 protein and IGFBP2 protein correctly, ELISA methods comprised human ErbB3 kit (DY348) and human IGFBP2 kit (DY674) (R&D Systems Europe, Ltd) were used. Human ErbB3 protein and human IGFBP2 proteins which were produced by genetic engineer technology were used as standard.

Antibody for detecting ERBB3 protein in ELISA assay:
1. Capture antibody: an antibody which could bind to SEQ ID NO: 2 (R&D Systems, MAB 3481).
2. Detection antibody: a biotinylated monoclone antibody which could bind to SEQ ID NO: 2 (R&D Systems, BAM348).

ELISA antibody for IGFBP2 proteins:
1. Capture antibody: an antibody which could bind to SEQ ID NO: 4 (R&D Systems, MAB6741).
2. Detection antibody: a biotinylated antibody, goat IgG, which could bind to SEQ ID NO: 4 (R&D Systems, BAF674).

Steps for operation:

(a) Both capture antibodies were diluted to the concentration of 4 mg/ml, and added 100 µl to each reaction well at room temperature for reacting overnight;

(b) The obtained serum were diluted (the average dilution rate 10-100×), and 100 µl diluted serum were added into each reaction well at room temperature for 2 hours;

(c) The diluted serum were removed and the reaction wells were washed by wash solution, then 2 mg/ml of 100 µl biotinylated detection antibodies were added into each reaction wells at room temperature for 2 hours;

(d) The reaction wells were washed again, and strptavidin-HRP which was included in the kit was added and reacted in dark at room temperature for 20 minutes;

(e) The reaction wells were washed again, the subtracts which was also included in the kit were added for reaction at room temperature for 20 minutes;

(f) The data were read by microplate reader at 450 nm and 540 nm and corrected by 540 nm absorption as background value. After correction, the true absorption values were obtained. Then, the concentration of ERBB3 proteins and IGFBP2 proteins were evaluated by comparing with the concentration of standard samples.

Serum samples were collected from 113 liver cancer patients and 111 non-liver cancer patients (including 47 cirrhosis patients, 64 chronic hepatitis B) underwent the concentration of ERBB3 and IGFBP2 in serum samples for liver cancer detection.

Figure 4:
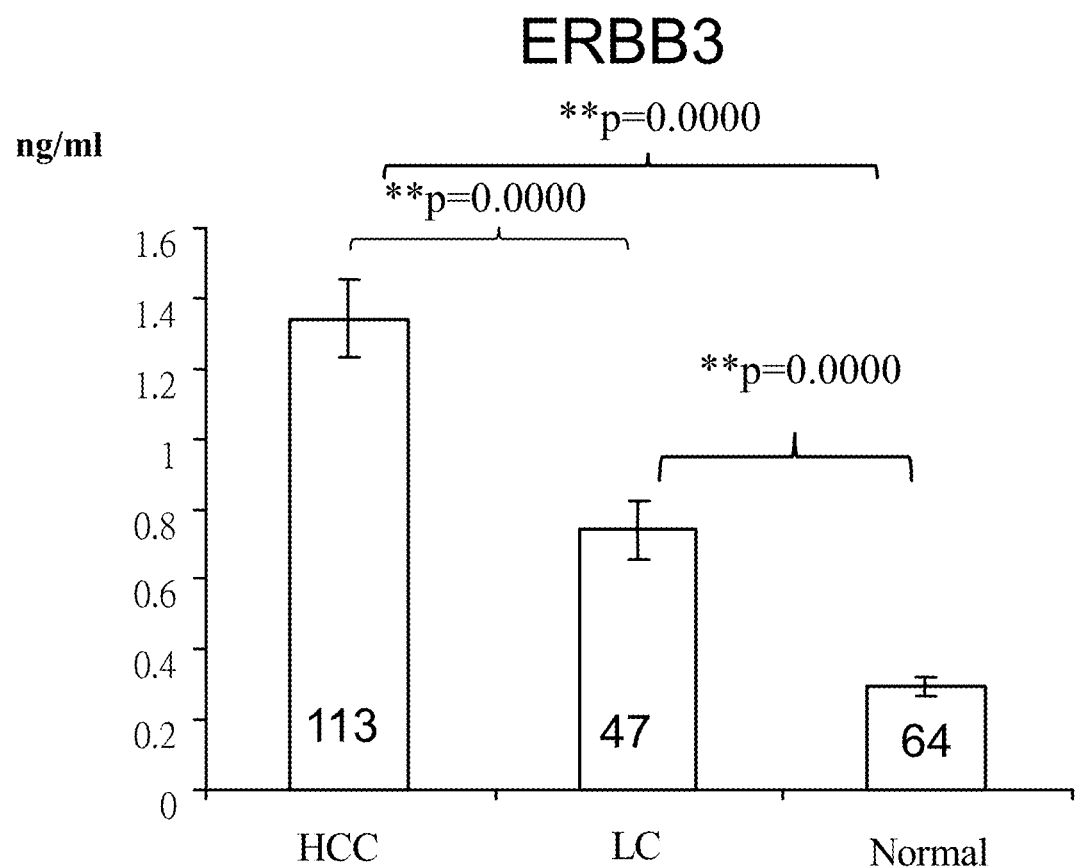
FIG. 4 is a chart showing different concentrations of ERBB3 proteins obtained from different tissues.
Figure 5A:
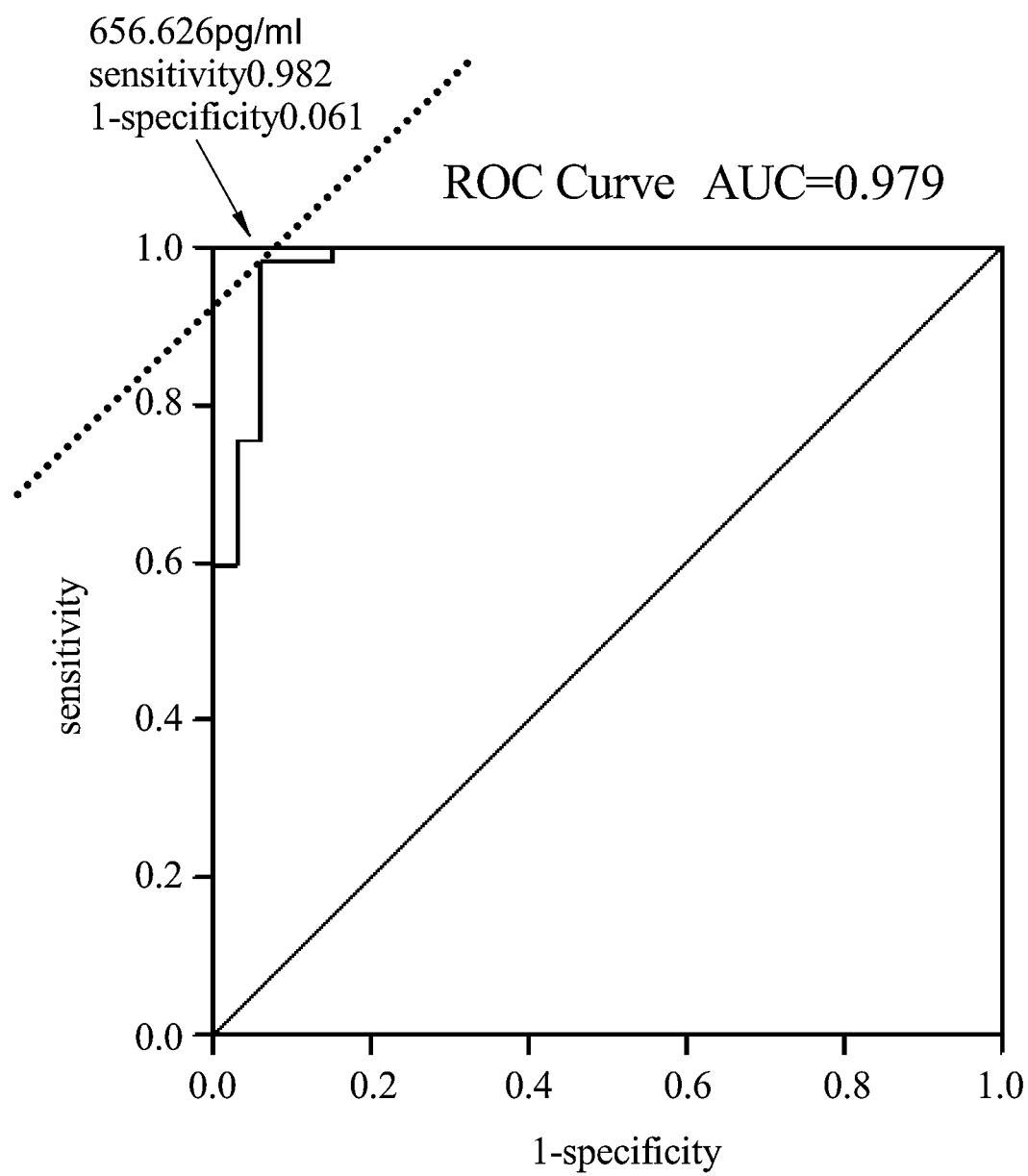
FIG. 5A is a chart showing ROC curve of serum ERBB3 discriminating hepatoma from non-hepatoma controls in the discovery group in accordance with the present invention.
Figure 5B:
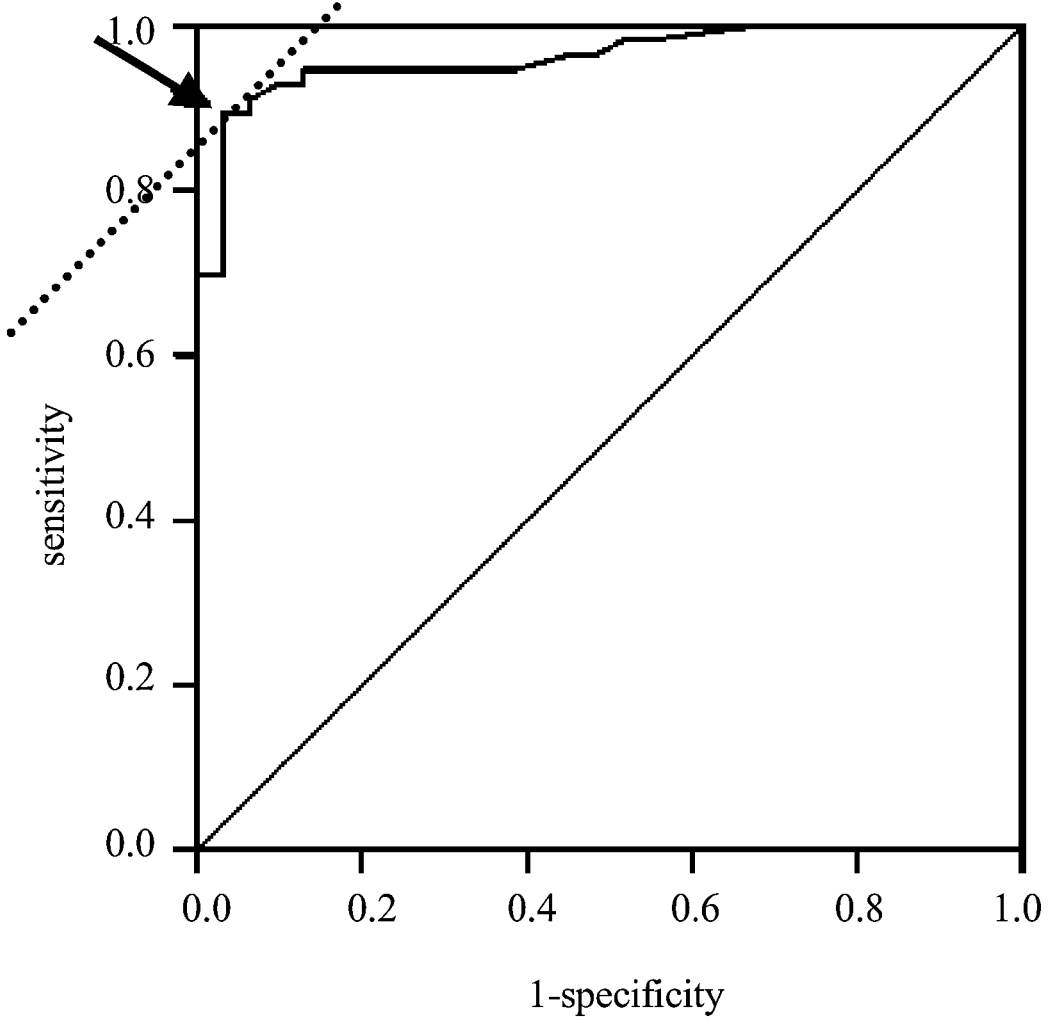
FIG. 5B is a chart showing ROC curve of serum ERBB3 discriminating hepatoma from non-hepatoma controls in the validation group in accordance with the present invention.
Figure 5C:
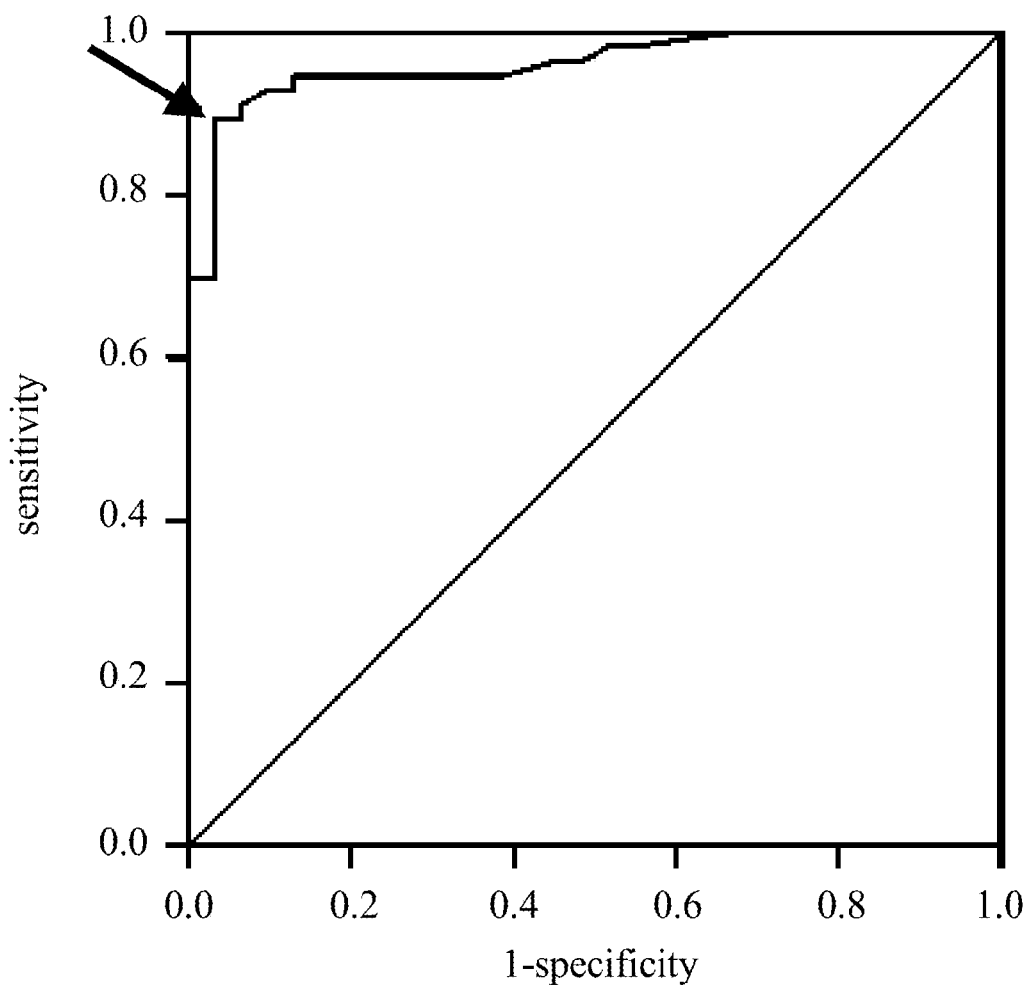
FIG. 5C is a chart showing ROC curve of serum ERBB3 discriminating hepatoma from non-hepatoma controls in the discovery and validation groups in accordance with the present invention.
Figure 6:
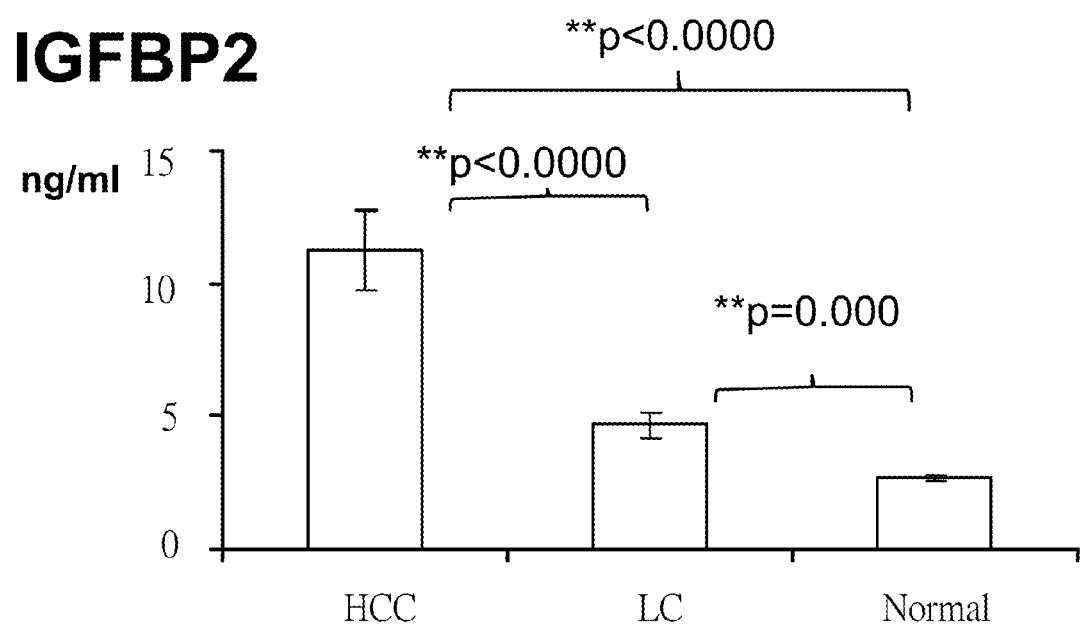
FIG. 6 is a chart showing different IGFBP2 concentrations in Example 1 obtained from different tissues.

With reference to FIGS. 4 to 6, the concentrations of serum ERBB3 protein and serum IGFBP2 protein in 113 liver cancer patients and 111 non-liver cancer patients were analyzed by student t-test to understand the difference. Results showed that false-positive values were less than 1/100 and p<0.01 were preliminarily selected for further analysis. The concentrations of serum ERBB3 proteins and serum IGFBP2 proteins, which showed a significant difference, were following analyzed by ROC curve analysis.

B. ROC curve analysis

To further understand whether ERBB3 protein and IGFBP2 protein were suitable for being markers for liver cancer detection, we provided another two group samples for each candidate markers for further check.

For IGFBP2 protein check experiment, there were 57 liver cancer patients and 35 non-liver cancer patients in Group I (taken as discovery group), and there were 56 liver cancer patients and 36 non-liver cancer patients in Group II (taken as validation group).

For ERBB3 protein check experiment, there were 56 liver cancer patients and 32 non-liver cancer but with hepatitis B patients in Group I (taken as discovery group), and there were 57 liver cancer patients and 32 non-liver cancer but with hepatitis B patients in Group II (taken as validation group). Results were shown in table 1 and table 2, respectively.

TABLE 1

Concentrations of IGFBP2 protein in serum

| | Group I (Discovery Group) | | | Group II (validation Group) | |
|---|---|---|---|---|---|
| | Liver cancer patient (ng/ml) | Non-liver cancer patient (ng/ml) | | Liver cancer patient (ng/ml) | Non-liver cancer patient (ng/ml) |
| 1 | 43.48484 | 37.16512915 | 1 | 101.4429 | 29.72011915 |
| 2 | 42.84814 | 27.8824984 | 2 | 67.78099 | 34.66665435 |
| 3 | 94.947 | 32.18498435 | 3 | 74.59434 | 29.72011915 |
| 4 | 51.20713 | 26.6626694 | 4 | 72.53931 | 26.6626694 |
| 5 | 94.23048 | 20.6265424 | 5 | 49.26238 | 20.02870635 |
| 6 | 102.898 | 36.538935 | 6 | 347.0552 | 25.4470416 |
| 7 | 113.2013 | 26.6626694 | 7 | 898.2424 | 26.6626694 |
| 8 | 66.43093 | 30.95045115 | 8 | 69.13526 | 38.42066835 |
| 9 | 47.32708 | 23.0283896 | 9 | 73.22327 | 36.538935 |
| 10 | 63.07414 | 31.5671926 | 10 | 61.07267 | 23.0283896 |
| 11 | 78.73277 | 12.352415 | 11 | 72.53931 | 19.4319206 |
| 12 | 175.1997 | 27.8824984 | 12 | 59.08066 | 32.8038264 |
| 13 | 99.99205 | 23.0283896 | 13 | 1059.827 | 40.3118544 |
| 14 | 32.80383 | 27.8824984 | 14 | 158.0795 | 23.0283896 |
| 15 | 29.72012 | 21.8253654 | 15 | 202.1783 | 29.72011915 |
| 16 | 73.22327 | 29.1065286 | 16 | 31.56719 | 31.5671926 |
| 17 | 118.4302 | 33.42371875 | 17 | 54.46938 | 42.21249315 |
| 18 | 150.8841 | 32.18498435 | 18 | 70.49373 | 21.22542875 |
| 19 | 61.73878 | 32.8038264 | 19 | 47.32708 | 25.4470416 |
| 20 | 58.41875 | 19.4319206 | 20 | 72.53931 | 35.91379115 |
| 21 | 176.8544 | 15.28382875 | 21 | 103.6272 | 21.22542875 |
| 22 | 84.30948 | 37.7923736 | 22 | 57.0981 | 21.22542875 |
| 23 | 46.04213 | 30.95045115 | 23 | 108.024 | 24.84080315 |
| 24 | 143.7737 | 14.6954454 | 24 | 49.90958 | 21.8253654 |
| 25 | 35.91379 | 36.538935 | 25 | 69.81397 | 21.22542875 |
| 26 | 37.16513 | 19.4319206 | 26 | 57.7579 | 28.49398835 |
| 27 | 116.183 | 21.22542875 | 27 | 35.91379 | 13.5218296 |
| 28 | 82.909 | 21.22542875 | 28 | 150.0898 | 26.05433035 |
| 29 | 792.7261 | 21.22542875 | 29 | 131.3431 | 22.42635235 |
| 30 | 76.65883 | 19.4319206 | 30 | 112.4586 | 30.95045115 |
| 31 | 115.436 | 67.7809926 | 31 | 142.9889 | 15.8732624 |
| 32 | 89.24425 | 14.10811235 | 32 | 283.8218 | 13.5218296 |
| 33 | 100.717 | 12.93659715 | 33 | 75.96962 | 30.33476 |
| 34 | 286.6897 | 17.64786515 | 34 | 38.42067 | 39.0500134 |
| 35 | 84.30948 | 15.8732624 | 35 | 162.1137 | 42.84814 |
| 36 | 43.48484 | | 36 | 785.7038 | 15.28382875 |
| 37 | 77.34909 | | 37 | 196.1848 | |
| 38 | 75.96962 | | 38 | 63.07414 | |
| 39 | 80.12064 | | 39 | 55.78164 | |
| 40 | 47.32708 | | 40 | 181.0094 | |
| 41 | 55.12499 | | 41 | 95.66457 | |
| 42 | 42.21249 | | 42 | 35.2897 | |
| 43 | 37.79237 | | 43 | 59.08066 | |
| 44 | 31.56719 | | 44 | 36.53894 | |
| 45 | 35.2897 | | 45 | 35.2897 | |
| 46 | 32.18498 | | 46 | 36.53894 | |
| 47 | 147.7134 | | 47 | 30.33476 | |
| 48 | 49.26238 | | 48 | 63.07414 | |
| 49 | 38.42067 | | 49 | 52.50888 | |
| 50 | 40.31185 | | 50 | 46.04213 | |
| 51 | 65.75747 | | 51 | 162.1137 | |
| 52 | 70.49373 | | 52 | 283.8218 | |
| 53 | 42.21249 | | 53 | 71.8564 | |
| 54 | 55.78164 | | 54 | 31.56719 | |
| 55 | 61.73878 | | 55 | 32.18498 | |
| 56 | 42.84814 | | 56 | 42.21249 | |
| 57 | 42.21249 | | | | |

TABLE 2

Concentrations of ERBB3 protein in serum

| | Group I (Discovery Group) | | | Group II (Validation Group) | |
|---|---|---|---|---|---|
| | Liver cancer patient (ng/ml) | Non-liver cancer patient (ng/ml) | | Liver cancer patient (ng/ml) | Non-liver cancer patient (ng/ml) |
| 1 | 819.626 | 136.066 | 1 | 768.546 | 1106.586 |
| 2 | 666.386 | 187.146 | 2 | 1023.946 | 289.306 |
| 3 | 1177.186 | 238.226 | 3 | 2505.266 | 289.306 |
| 4 | 2403.106 | 187.146 | 4 | 1381.506 | 340.386 |
| 5 | 1279.346 | 289.306 | 5 | 1892.306 | 187.146 |
| 6 | 921.786 | 136.066 | 6 | 1483.666 | 646.866 |
| 7 | 1483.666 | 289.306 | 7 | 1126.106 | 391.466 |
| 8 | 1534.746 | 62.346 | 8 | 921.786 | 62.346 |
| 9 | 870.706 | 442.546 | 9 | 2096.626 | 289.306 |
| 10 | 819.626 | 544.706 | 10 | 2249.866 | 136.066 |
| 11 | 1279.346 | 902.266 | 11 | 768.546 | 187.146 |
| 12 | 1075.026 | 187.146 | 12 | 870.706 | 62.346 |
| 13 | 1687.986 | 595.786 | 13 | 870.706 | 136.066 |
| 14 | 7306.786 | 136.066 | 14 | 1177.186 | 62.346 |
| 15 | 1687.986 | 271.84 | 15 | 972.866 | 238.226 |
| 16 | 819.626 | 271.84 | 16 | 1790.146 | 339.2 |
| 17 | 1228.266 | 372.88 | 17 | 1228.266 | 137.12 |
| 18 | 666.386 | 406.56 | 18 | 1841.226 | 305.52 |
| 19 | 1177.186 | 406.56 | 19 | 1177.186 | 69.76 |
| 20 | 2096.626 | 137.12 | 20 | 1075.026 | 69.76 |
| 21 | 972.866 | 810.72 | 21 | 1432.586 | 574.96 |
| 22 | 541.586 | 204.48 | 22 | 1279.346 | 103.44 |
| 23 | 1330.426 | 642.32 | 23 | 921.786 | 204.48 |
| 24 | 870.706 | 305.52 | 24 | 1841.226 | 36.08 |
| 25 | 1687.986 | 372.88 | 25 | 1126.106 | 473.92 |
| 26 | 768.546 | 271.84 | 26 | 1126.106 | 204.48 |
| 27 | 870.706 | 541.28 | 27 | 1177.186 | 238.16 |
| 28 | 972.866 | 137.12 | 28 | 1177.186 | 473.92 |
| 29 | 1432.586 | 204.48 | 29 | 1330.426 | 170.8 |
| 30 | 666.386 | 58.16 | 30 | 666.386 | 291.68 |
| 31 | 870.706 | 204.11 | 31 | 768.546 | 116.54 |
| 32 | 921.786 | 466.82 | 32 | 921.786 | 320.87 |
| 33 | 1381.506 | | 33 | 666.386 | |
| 34 | 1228.266 | | 34 | 768.546 | |
| 35 | 768.546 | | 35 | 819.626 | |
| 36 | 8685.946 | | 36 | 921.786 | |
| 37 | 1330.426 | | 37 | 1023.946 | |
| 38 | 717.466 | | 38 | 870.706 | |
| 39 | 1075.026 | | 39 | 1177.186 | |
| 40 | 1177.186 | | 40 | 5825.466 | |
| 41 | 1636.906 | | 41 | 1177.186 | |
| 42 | 819.626 | | 42 | 1330.426 | |
| 43 | 1177.186 | | 43 | 768.546 | |
| 44 | 717.466 | | 44 | 1177.186 | |
| 45 | 1841.226 | | 45 | 972.866 | |
| 46 | 972.866 | | 46 | 972.866 | |
| 47 | 972.866 | | 47 | 768.546 | |
| 48 | 1023.946 | | 48 | 1075.026 | |
| 49 | 819.626 | | 49 | 819.626 | |
| 50 | 1652.72 | | 50 | 305.52 | |
| 51 | 608.64 | | 51 | 4650.24 | |
| 52 | 507.6 | | 52 | 1955.84 | |
| 53 | 2730.48 | | 53 | 1046.48 | |
| 54 | 878.08 | | 54 | 574.96 | |
| 55 | 676 | | 55 | 2797.84 | |
| 56 | 1248.56 | | 56 | 204.48 | |
| | | | 57 | 271.84 | |

The concentrations data shown in table 1 and table 2 were further described as follow:

(1) Results showed that ERBB3 proteins was a proper biomarker for liver cancer (hepatoma) detection (i) With reference to FIG. 4, the ERBB3 protein concentration in serum in 113 liver cancer patients were higher than 47 cirrhosis without liver cancer patients (p<0.0001, student's t-test), and also higher than 64 chronic hepatitis B patients (p<0.0001, student's t-test).

(ii) With reference to FIG. 5A, the AUC values of Group I which had 56 liver cancer patients and 32 non-liver cancer but with hepatitis B patients was 97.9%.

(iii) With reference to FIG. 5B, the AUC values of Group II which had 57 liver cancer patients and 32 non-liver cancer but with hepatitis B patients was 96.1%.

(iv) With reference to FIG. 5C, analyzing by the cut-off value of Youden index, the sensitivity value for detecting liver cancer was 93.8% after combining Group I and Group II patient samples, and the specificity value was 5.3%. Similarly, by analyzing AFP in serum, the AUC values of the liver cancer patients and non-liver cancer patients were 84.3% after combining the two groups, but the AUC values of ERBB3 proteins only were 9.7%.

The above results showed that analyzed by the concentration of ERBB3 protein in serum is more sensitive than analyzed by AFP in serum. Therefore, it is powerful to use ERBB3 protein as a biomarker for detecting liver cancer.

(2) Results showed that IGFBP2 proteins was a proper biomarker for liver cancer (hepatoma) detection (i) With reference to FIG. 6, the concentration of IGFBP2 protein in serum in 113 liver cancer patients were higher than 47 cirrhosis without liver cancer patients (p<0.001, student's t-test), and also higher than 64 chronic hepatitis B patients (p<0.001, student's t-test).

Figure 7A:
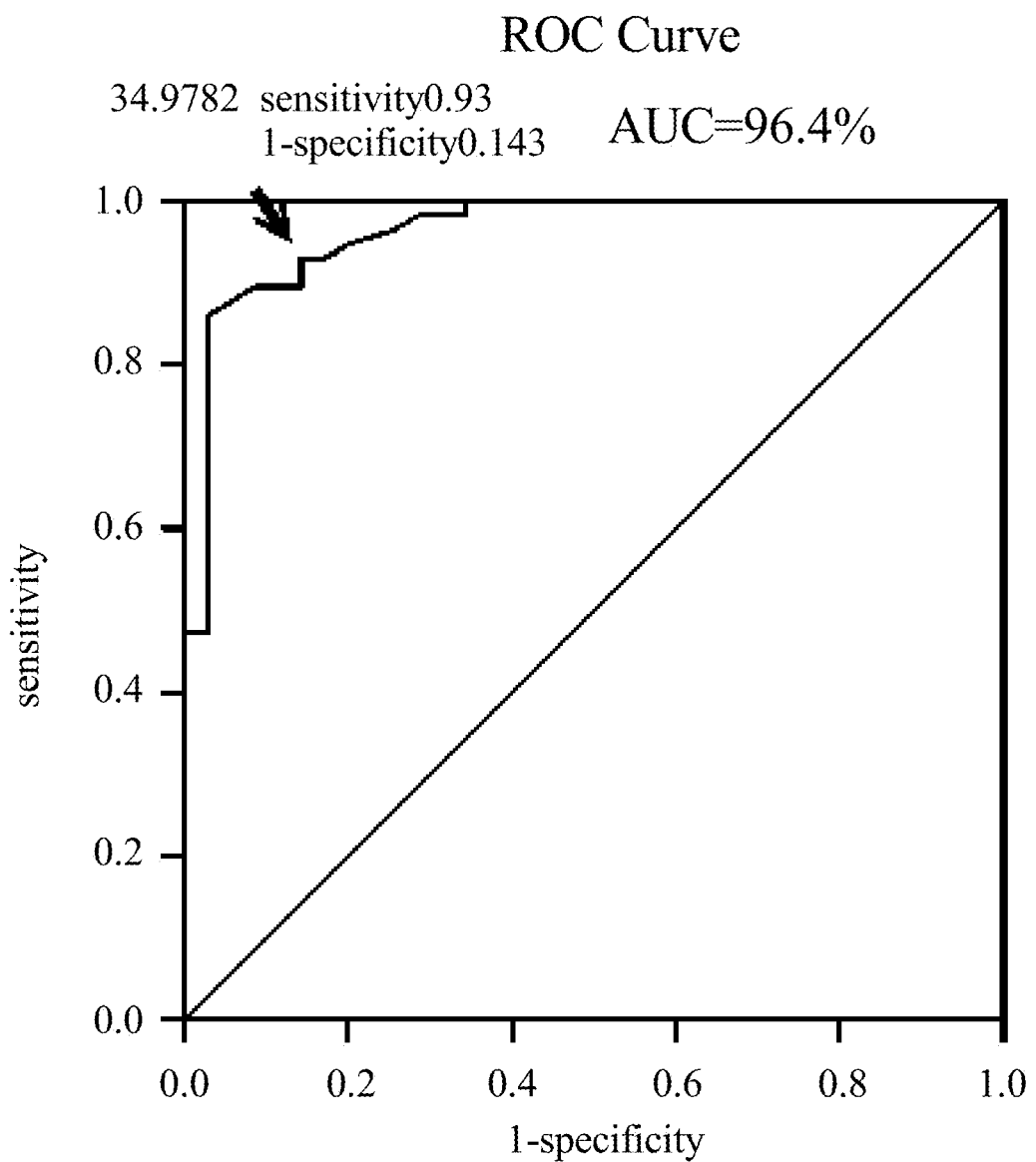
FIG. 7A is a chart showing ROC curve of serum IGFBP2 discriminating hepatoma from non-hepatoma controls in the discovery group in accordance with the present invention.

(ii) With reference to FIG. 7A, the AUC value of the serum in Group I which had 57 liver cancer patients and 35 hepatitis B without liver cancer patients were 96.4%.

Figure 7B:
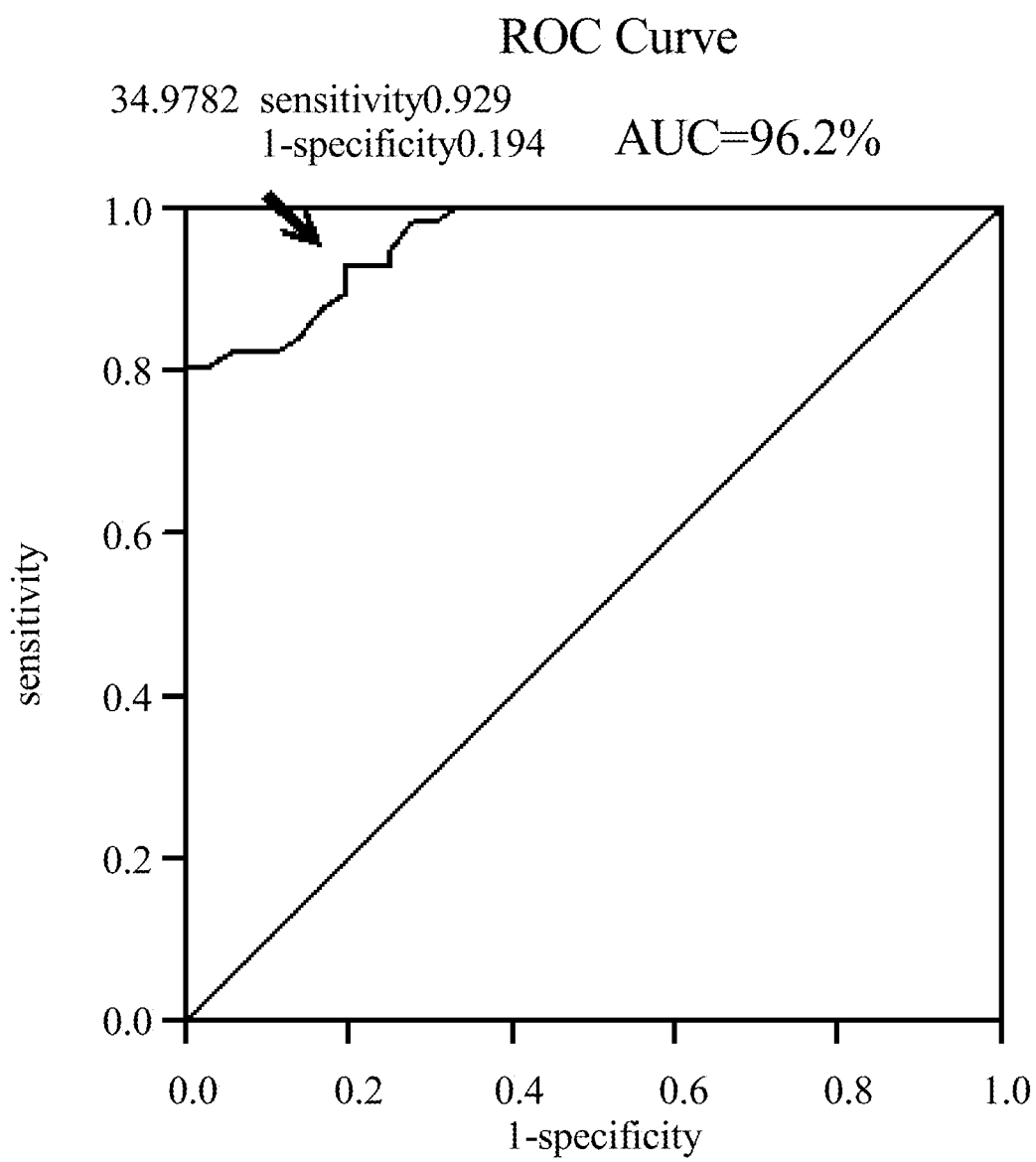
FIG. 7B is a chart showing ROC curve of serum IGFBP2 discriminating hepatoma from non-hepatoma controls in the validation group in accordance with the present invention.

(iii) With reference to FIG. 7B, the AUC value of the serum in Group II which had 56 liver cancer patients and 36 hepatitis B without liver cancer patients were 96.24%.

Figure 7C:
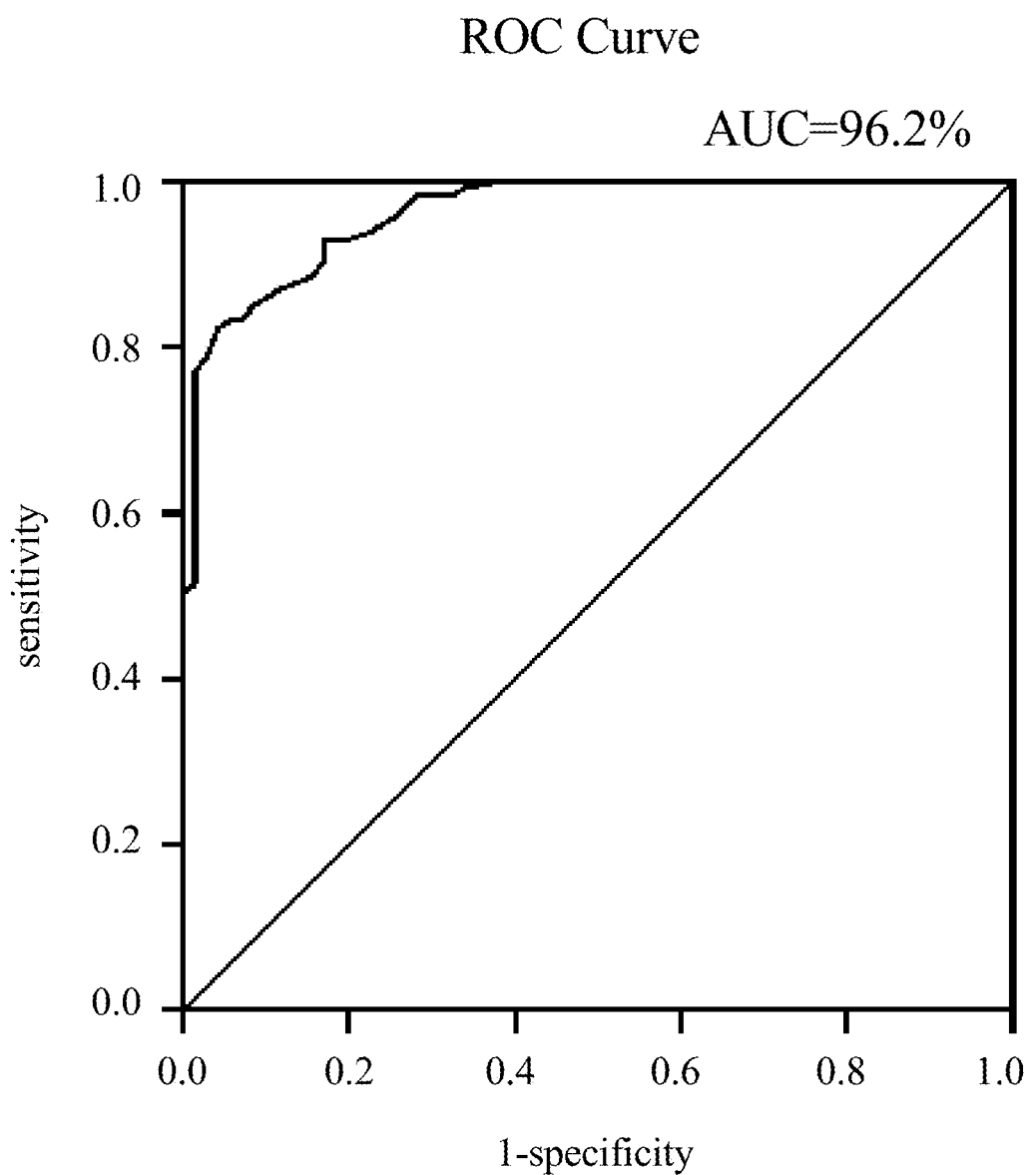
FIG. 7C is a chart showing ROC curve of serum IGFBP2 discriminating hepatoma from non-hepatoma controls in the discovery and validation groups in accordance with the present invention.

(iv) With reference to FIG. 7C, the AUC value was 96.2% after combing Group I and Group II patient samples. However, by detecting AFP in serum, the AUC values of the liver cancer patients and non-liver cancer patients were 71.5% after combining the two Groups. Therefore, detecting by the concentration of IGFBP2 in serum to identify liver cancer patients and non-liver cancer with hepatitis B patients were more sensitive and specificities than detecting by AFP values.

The above results showed that analyzed by the concentration of IGFBP2 protein in serum is more sensitive than analyzed by AFP values in serum. Therefore, it is powerful to use IGFPB2 protein as a biomarker for detecting liver cancer.

Combination detection of AFP, ERBB3 protein and IGFBP2 protein in serum to increase the sensitivity and specificity of liver cancer detection (i) The AUC values of AFP, ERBB3 and IGFBP2 were 84.3%, 9.7% and 96.2%, respectively.

Figure 8A:
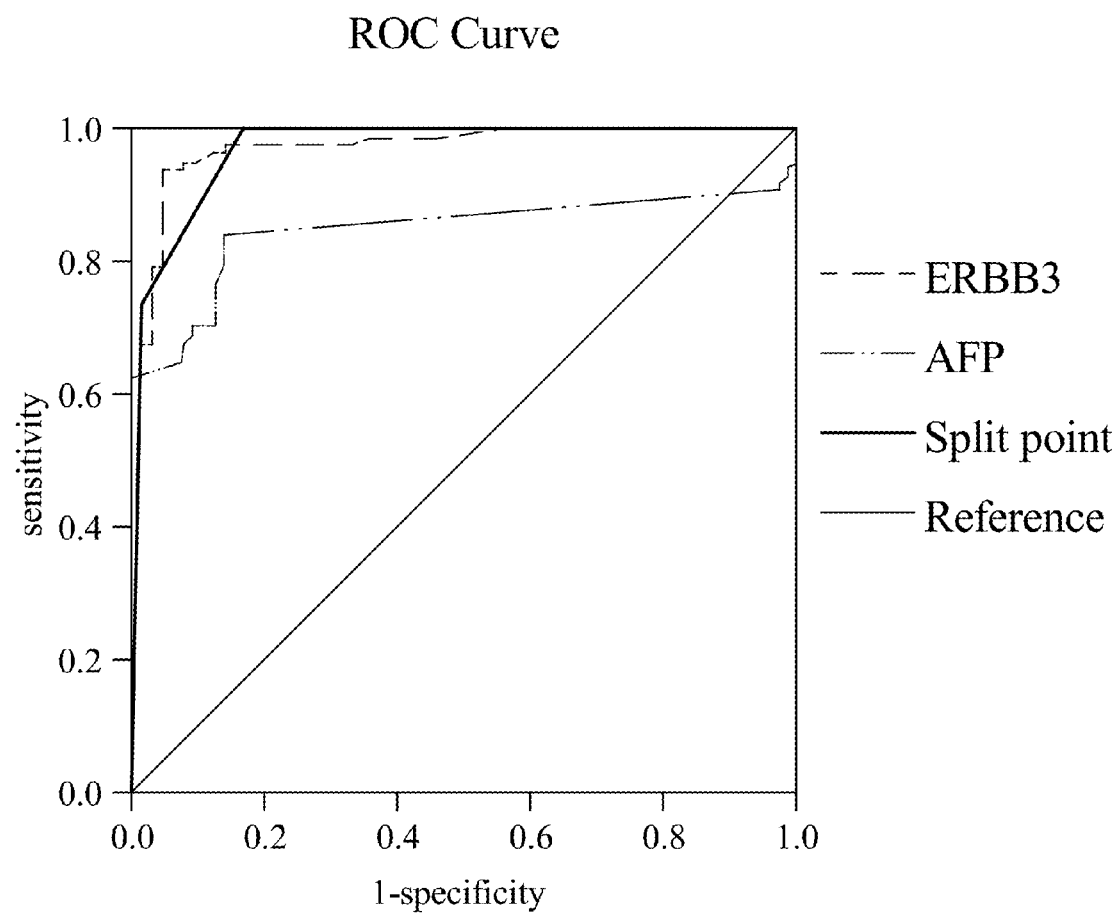
FIG. 8A is a chart showing ROC curve of serum ERBB3, AFP, or combined ERBB3 and AFP in discriminating hepatoma from non-hepatoma controls in one of the present embodiment in accordance with the present invention.
Figure 8B:
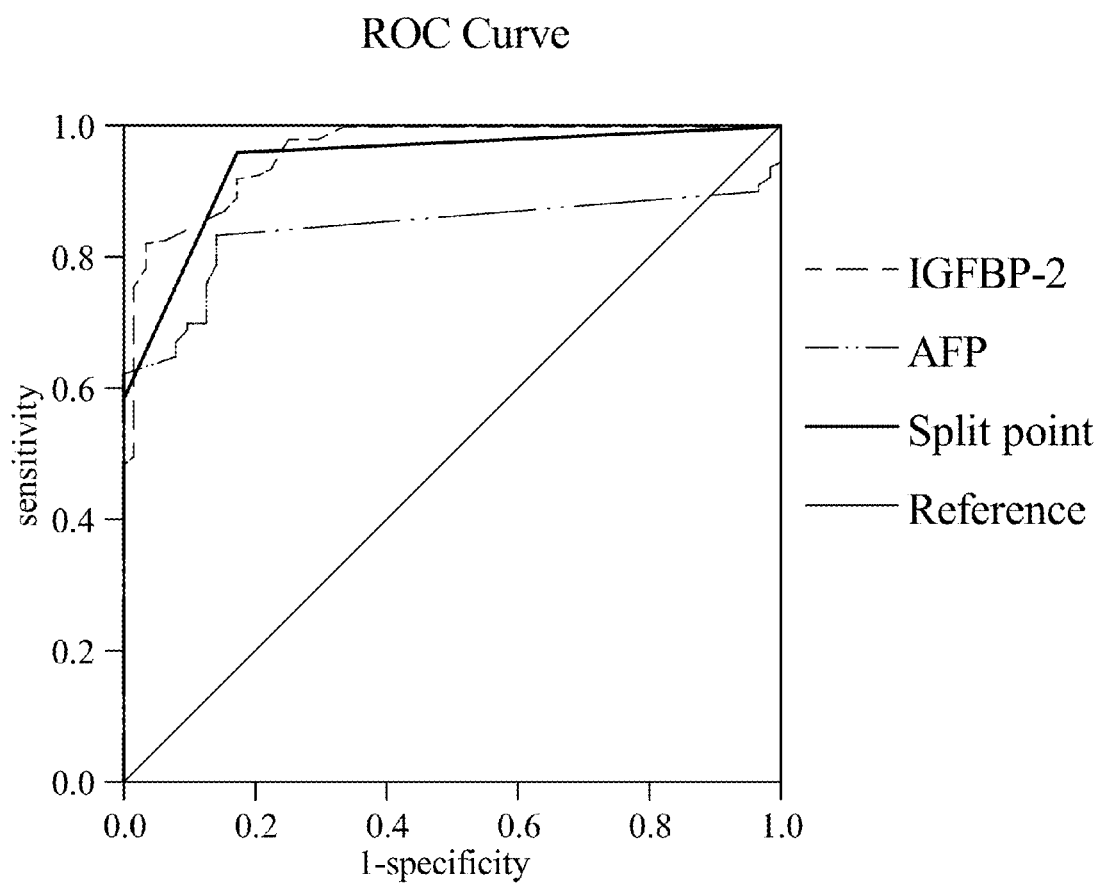
FIG. 8B is a chart showing ROC curve of serum IGFBP2, AFP, or combined IGFBP2 and AFP in discriminating hepatoma from non-hepatoma controls in one of the present embodiment in accordance with the present invention.
Figure 8C:
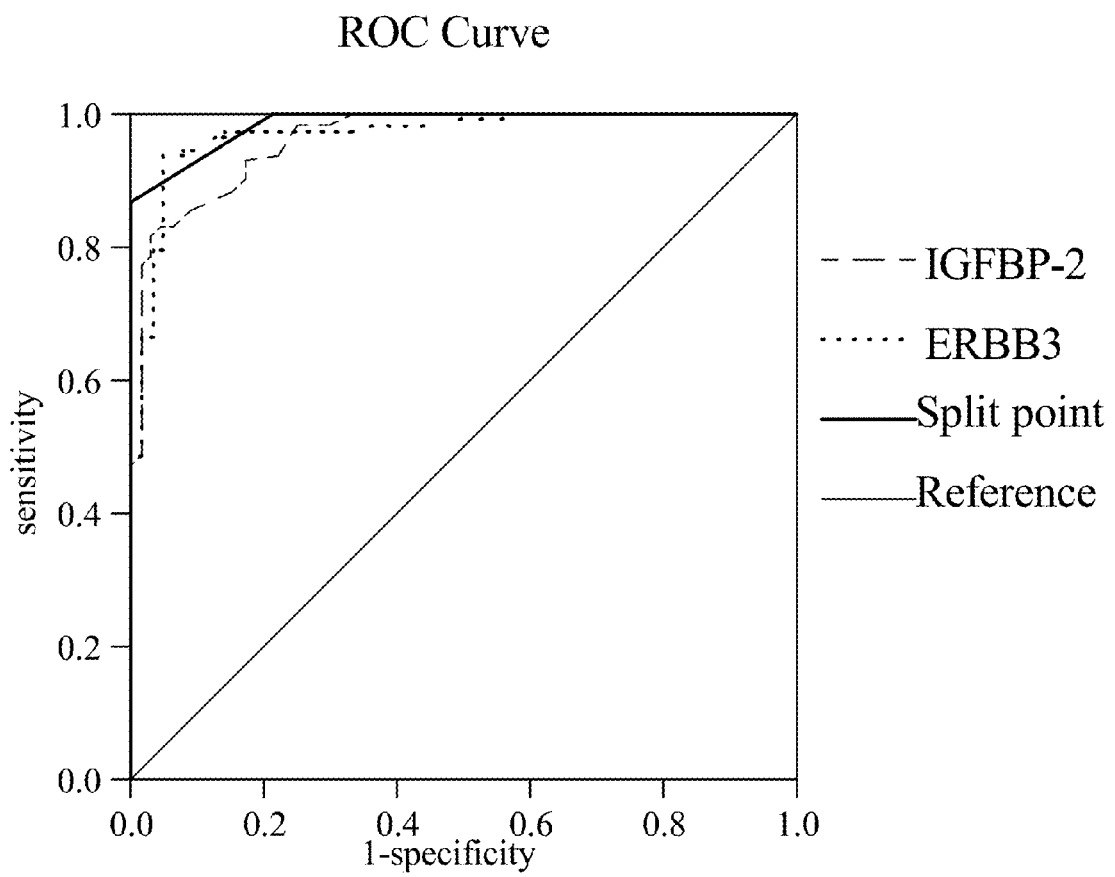
FIG. 8C is a chart showing ROC curve of serum IGFBP2, ERBB3, or combined IGFBP2 and ERBB3 in discriminating hepatoma from non-hepatoma controls in one of the present embodiment in accordance with the present invention.
Figure 8D:
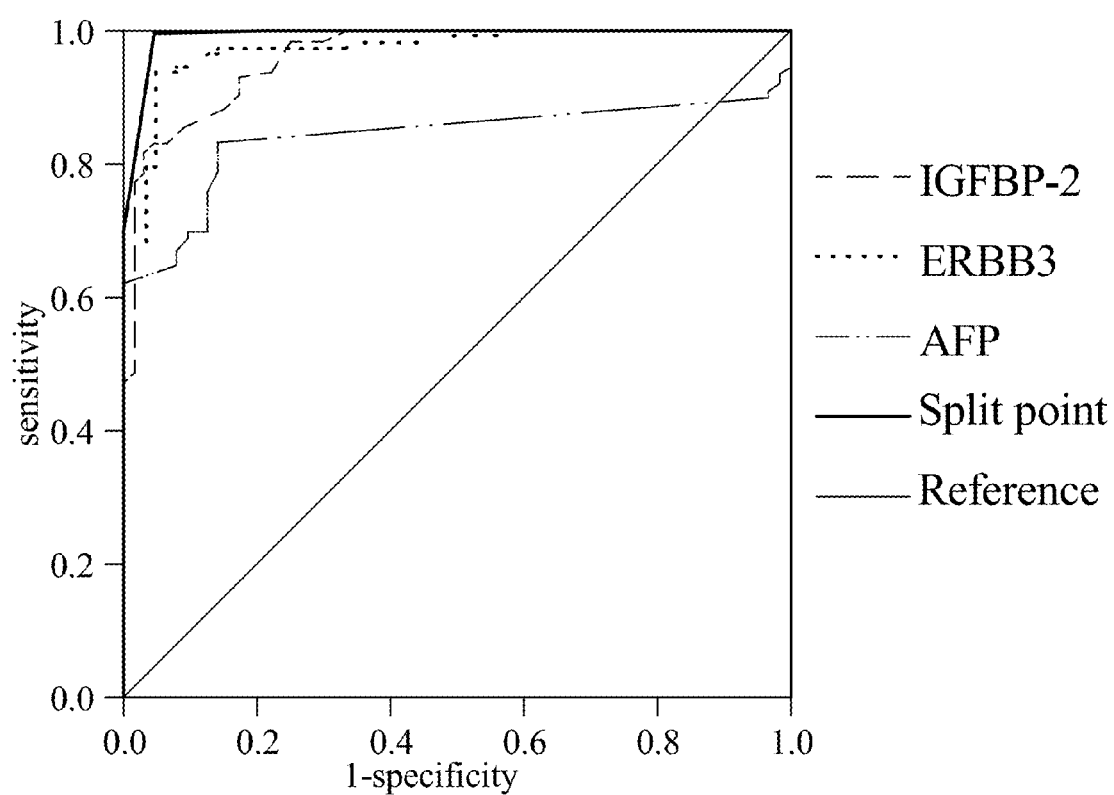
FIG. 8D is a chart showing ROC curve of serum ERBB3, IGFBP2, AFP, or combined ERBB3, IGFBP2, and AFP in discriminating hepatoma from non-hepatoma controls in one of the present embodiment in accordance with the present invention.

(ii) With reference to FIGS. 8A and 8B, the AUC values of AFP+ERBB3 and AFP+IGFBP2 were 96.9% and 94.5%, respectively. With reference to FIG. 8C, the AUC value of ERBB3+IGFBP2 was 98.5%. Furthermore, with reference to FIG. 8D, the AUC value of AFP+ERBB3+IGFBP2 was 99.1%. Therefore, to increase the sensitivity and specificity to almost 100%, it is very useful to combine AFP value, ERBB3 value and IGFBP2 value for diagnosis of hepatoma.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. A kit for detecting liver cancer, consisting of an antibody for binding ERBB3; and an antibody for binding IGFBP2, wherein the antibodies are for detecting liver cancer.

2. The kit of claim 1, wherein ERBB3 comprises SEQ ID NO: 2.

3. The kit of claim 1, wherein IGFBP2 comprises SEQ ID NO: 4.

4. The kit of claim 1, wherein at least one of the antibodies is a polyclonal antibody, a monoclonal antibody, or an antigen binding fragment thereof.

5. The kit of claim 4, wherein at least one of the antibodies is IgG.

6. The kit of claim 1, wherein at least one of the antibodies is labeled.

7. The kit of claim 1, which further comprises an antibody for detecting alpha-fetoprotein.

8. The kit of claim 1, wherein said ERBB3 and IGFBP2 are in a serum sample.

* * * * *